(12) United States Patent
Ketchum (10) Patent No.: US 12,275,923 B2
(45) Date of Patent: Apr. 15, 2025

(54) SYSTEMS AND METHODS FOR CONTROLLING ATTENUATION IN A FERMENTATION PROCESS

(71) Applicant: Rhinegeist, LLC, Cincinnati, OH (US)

(72) Inventor: Nicholas Ketchum, Cincinnati, OH (US)

(73) Assignee: Rhinegeist, LLC, Cincinnati, OH (US)

( * ) Notice: Subject to any disclaimer, the term of this patent is extended or adjusted under 35 U.S.C. 154(b) by 885 days.

(21) Appl. No.: 17/199,911

(22) Filed: Mar. 12, 2021

(65) Prior Publication Data

US 2021/0284939 A1    Sep. 16, 2021

Related U.S. Application Data

(60) Provisional application No. 63/135,147, filed on Jan. 8, 2021, provisional application No. 62/988,655, filed on Mar. 12, 2020.

(51) Int. Cl.

| | | |
|---|---|---|
| *C12C 11/00* | (2006.01) | |
| *C12C 5/00* | (2006.01) | |
| *C12H 1/00* | (2006.01) | |
| *C12Q 1/18* | (2006.01) | |
| *C12Q 1/6895* | (2018.01) | |

(52) U.S. Cl.
CPC ............. *C12C 11/00* (2013.01); *C12C 5/00* (2013.01); *C12H 1/003* (2013.01); *C12Q 1/18* (2013.01); *C12Q 1/6895* (2013.01)

(58) Field of Classification Search
CPC ......... C12Q 1/18; C12Q 1/6895; C12C 5/00; C12C 11/00; C12C 11/003; C12C 11/02; C12C 11/07; C12C 12/002; C12C 12/004; C12C 12/006; C12C 12/008; C12C 12/02; C12C 12/04; C12N 1/14; C12N 1/18; C12N 1/16; C12N 1/36; C12H 1/003; C12H 3/00; C12G 1/00; C12G 1/14; C12G 3/00; C12G 3/02; C12G 3/025; C12G 3/026; C12G 3/08
See application file for complete search history.

(56) References Cited

U.S. PATENT DOCUMENTS

| | | |
|---|---|---|
| 4,418,150 A | 11/1983 | Gunge |
| 4,806,472 A | 2/1989 | de Louvencourt et al. |
| 4,910,144 A | 3/1990 | Saito et al. |
| 5,783,183 A | 7/1998 | Langeveld et al. |
| 2005/0233032 A1 | 10/2005 | Savard et al. |
| 2018/0327733 A1 | 11/2018 | Denby et al. |

OTHER PUBLICATIONS

Akiyama et al JP-63183506-A machine translation Jul. 28, 1988 (Year: 1988).*
Akiyama et al JP-63183506-A original document with Abstract (Year: 1988).*

(Continued)

*Primary Examiner* — Vera Stulii
(74) *Attorney, Agent, or Firm* — Frost Brown Todd LLP; Vance V. VanDrake, III; Alexander J. Johnson (57) ABSTRACT

A method of controlling attenuation in a fermentation process includes culturing a fungus in a medium to produce a fermented liquid and adding a killer toxin to the fermented liquid. The killer toxin is added in an amount effective to deactivate the fungus.

12 Claims, 5 Drawing Sheets

(56) References Cited

OTHER PUBLICATIONS

Young, "The genetic manipulation of killer character into brewing yeast," Journal of the Institute of Brewing. Institute of Brewing (Great Britain), Sep. 1981, 87(5):292-295, Retrieved from: https://europepmc.org/article/agr/ind82060593 (4 pages).

Hammond et al., "Fermentation Properties of Brewing Yeast With Killer Character," Journal of the Institute of Brewing, 90: 167-177 (1984), Retrieved from: https://onlinelibrary.wiley.com/doi/abs/10.1002/j.2050-0416.1984.tb04258.x (11 pages).

Radler et al., "Killer Toxins of Yeasts: Inhibitors of Fermentation and Their Adsorption," J Food Prot. Mar. 1987, 50 (3):234-238, Retrieved from: https://www.ncbi.nlm.nih.gov/pubmed/30965426 (5 pages).

Atkinson, "Technical Opportunities for Malting and Brewing in the '90's," Journal of the Institute of Brewing, 94: 261-272 (1988), Retrieved from: https://onlinelibrary.wiley.com/doi/abs/10.1002/j.2050-0416.1988.tb04583.x (12 pages).

Ciani et al., "Killer Toxin of Kluyveromyces phaffii DBVPG 6076 as a Biopreservative Agent to Control Apiculate Wine Yeasts," Appl Environ Microbiol. Jul. 2001; 67(7): 30583063, Retrieved from: https://www.ncbi.nlm.nih.gov/pmc/articles/PMC92981/ (6 pages).

Vaughan, "Enhancing the Microbiological Stability of Malt and Beer a Review," Journal of the Institute of Brewing, 111: 355-371 (2005), Retrieved from: https://onlinelibrary.wiley.com/doi/abs/10.1002/j.2050-0416.2005.tb00221.x (17 pages).

Comitini et al, "Kluyveromyces wickerhamii killer toxin: purification and activity towards Brettanomyces/Dekkera yeasts in grape must," FEMS Microbiol Lett, Jan. 17, 2011, vol. 316, No. 1, pp. 77-82, Retrieved from https://pubmed.ncbi.nlm.nih.gov/21204930/ (6 pages).

Oro et al., "Evaluation of damage induced by Kwkt and Pikt zymocins against Brettanomyces/Dekkera spoilage yeast, as compared to sulphur dioxide," J Appl Microbiol, 121: 207-214 (2016), Retrieved from: https://sfamjournals.onlinelibrary.wiley.com/doi/full/10.1111/jam.13121 (8 pages).

Comitini et al, "Pichia anomala and Kluyveromyces wickerhamii killer toxins as new tools against Dekkera/Brettanomyces spoilage yeasts," FEMS Microbiology Letters, 238: 235-240 (2004), Retrieved from: https://onlinelibrary.wiley.com/doi/abs/10.1111/j.1574-6968.2004.tb09761.x?SID=nlm%3Apubmed (6 pages).

Yap et al, "The incidence of killer activity of non-Saccharomyces yeasts towards indigenous yeast species of grape must: potential application in wine fermentation," Journal of Applied Microbiology, 89: 381-389 (2000), Retrieved from: https://sfamjournals.onlinelibrary.wiley.com/doi/full/10.1046/j.1365-2672.2000.01124.x?SID=nlm%3Apubmed (9 pages).

Zimmermann, M. et al.,(1996) "Protoplast Fusion of Yeasts," chapter 2 of "Nonconventional Yeasts in Biotechnology," Springer, Berlin, Heidelberg, https://doi.org/10.1007/978-3-642-79856-6_2 (17 pages).

Maule, A.P. et al.; Strains of yeast lethal to brewery yeasts; Journal of the Institute of Brewing, vol. 72, 1973; pp. 137-141.

Breinig, F. et al.; Dissecting toxin immunity in virus-infected killer yeast uncovers an intrinsic strategy of self-protection; Proceedings of the National Academy of Sciences, vol. 103, No. 10; Mar. 7, 2006; pp. 3810-3815.

Eiden-Plach, A. et al., Viral Preprotoxin Signal Sequence Allows Efficient Secretion of Green Fluorescent Protein by Candida glabrata, Pichia pastoris, Saccharomyces cerevisiae, and Schizosaccharomyces pombe; Applied and Environmental Microbiology, vol. 7, No. 2; Feb. 2004; pp. 961-966.

El-Banna, A. A., et al.; Yeasts Producing Killer Toxins: An Overview; Alex. J. Fd. Sci. & Technol., vol. 8, No. 2; Dec. 30, 2011; pp. 41-53.

Shalsh et al., Optimization of the Protoplast Fusion Conditions of Saccharomyces cerevisiae and Pichia stipitis for Improvement of Bioethanol Production from Biomass; Asian Journal of Biological Sciences, vol. 9, Nos. 1-2; Mar. 15, 2016; pp. 10-18.

Serviene, E. et al., Screening the Budding Yeast Genome Reveals Unique Factors Affecting K2 Toxin Susceptibility; PLoS ONE, vol. 7 No. 12; Dec. 5, 2012; pp. 1-13.

Ryan O. et al.; CRISPR-Cas9 Genome Engineering in Saccharomyces cerevisiae Cells; Cold Spring Harbor Protocols, Weizmann Institute of Science; Jun. 1, 2016; pp. 525-533.

Pfeiffer, P., & Radler, F.; Comparison of the killer toxin of several yeasts and the purification of a toxin of type K2; Archives of Microbiology, vol. 137; 1984; pp. 357-361.

Karbalaei, M. et al., Pichia pastoris: A highly successful expression system for optimal synthesis of heterologous proteins; Journal of Cellular Physiology, vol. 235, Jan. 9, 2020; 5867-5881.

Liu, Z. et al.; Different Expression Systems for Production of Recombinant Proteins in Saccharomyces cerevisiae; Biotechnology and Bioengineering, vol. 109, No. 5); May 2012; pp. 1259-1268.

Schmitt, M. J. et al.; K28 , A Unique Double-Stranded RNA Killer Virus of Saccharomyces cerevisiae; Molecular and Cellular Biology, vol. 10 No. 9; Sep. 1990; pp. 4807-4815.

Emerson, J. B. et al.; Schrodinger's microbes: Tools for distinguishing the living from the dead in microbial ecosystems, Microbiome, vol. 5, No. 86; 2017; 23 pages.

Denby, C.M. et al. Industrial brewing yeast engineered for the production of primary flavor determinants in hopped peer; Natural Communications vol. 9, No. 965; 2018; 10 pages.

Maqueda, M. et al.; Characterization, Ecological Distribution, and Population Dynamics of Saccharomyces sensu Stricto Killer Yeasts in the Spontaneous Grape Must Fermentations of Southwestern Spain; Applied and Environmental Microbiology, vol. 78, No. 3; Feb. 2012; pp. 735-743 (2012).

Maqueda, M. et al.; Wine yeast molecular typing using a simplified method for simultaneously extracting mtDNA, nuclear DNA and virus dsRNA; Food Microbiology, vol. 27; 2010; pp. 205-209.

Meier-dörnberg, T. et al.; Incidence of Saccharomyces cerevisiae var. diastaticus in the Beverage Industry: Cases of Contamination, 2008-2017; MBAA Technical Quarterly, vol. 54, No. 4; 2017; pp. 140-148.

Meier-Dörnberg, T. et al., Saccharomyces cerevisiae variety diastaticus friend or foe ?-spoilage potential and brewing ability of different Saccharomyces cerevisiae variety diastaticus yeast isolates by genetic, phenotypic and physiological characterization; FEMS Yeast Research, vol. 18, No. 4; 2018; pp. 1-27.

Melvydas, V. et al., A Novel Saccharomyces cerevisiae Killer Strain Secreting the X Factor Related to Killer Activity and Inhibition of S. cerevisiae K1, K2 and K28 Killer Toxins; Indian Journal of Microbiology, vol. 56, No. 3; Jul.-Sep. 2016; pp. 335-343.

Meškauskas, A., & Čitavičius, D.; The K2-type killer toxin- and immunity-encoding region from Saccharomyces cerevisiae: structure and expression in yeast; Gene, vol. 111; 1992; pp. 135-139.

Mohamudha, P., & Ayesha, B.; Production and effect of killer toxin by Saccharomyces cerevisiae on sensitive yeast and fungal pathogens; International Journal of Pharmaceutical Sciences Review and Research, vol. 3, No. 1; Aug. 2010; pp. 127-129.

Capece, A. et al.; Conventional and non-conventional yeasts in beer production; Fermentation, vol. 4, No. 38; 2018; 11 pages.

Ramirez, M. et al.; New insights into the genome organization of yeast killer viruses based on "atypical" killer strains characterized by high-throughput sequencing, Toxins, vol. 9, No. 292; 2017; 21 pages.

Rodríguez-Cousiño, N. et al.; Relationships and Evolution of Double-Stranded RNA Totiviruses of Yeasts Inferred from Analysis of L-A-2 and L-BC Variants in Wine Yeast Strain Populations; Applied and Environmental Microbiology, vol. 33, No. 4; Feb. 2017; pp. 1-18.

Schmitt, M. J. et al.; Yeast viral killer toxins: lethality and self-protection; Nature Reviews, Microbiology, vol. 4, No. 3, 212-221; Mar. 2006; pp. 212-221.

Schmitt, M. J., et al.; Viral induced yeast apoptosis, Biochimica et Biophysica Acta 1783; 2008; pp. 1413-1417.

Schmitt, M. J. et al.; Sequence of the M28 dsRNA: Preprotoxin is processed to an α/β heterodimeric protein toxin; Virology, vol. 213, No. 2; 1995; pp. 341-351.

Valsaraj, P. et al., "Biocontrol of yeast spoilage in selected food and beverages by yeast mycocin," Research Article, Acta Biologica (56) References Cited

OTHER PUBLICATIONS

Indica, 2012, Assn. for the Advancement of Biodiversity Science, pp. 109-112, Manipal, Karnataka, India.
Zhong, V. et al.,(2022) "Killer Toxins for the Control of Diastatic Yeasts in Brewing," Dept. of Biol. Sci., Univ. of Idaho, Moscow, ID; Rhinegiest Brewery, Cincinnati, OH; https://doi.org/10.1101/2022.10.17.512474 (10 pages).

* cited by examiner

SYSTEMS AND METHODS FOR CONTROLLING ATTENUATION IN A FERMENTATION PROCESS

CROSS REFERENCE TO RELATED APPLICATIONS

This application claims the priority benefit of U.S. Provisional Patent Application No. 63/135,147, filed Jan. 8, 2021, and U.S. Provisional Patent Application No. 62/988,655, filed Mar. 12, 2020, each of which is hereby incorporated herein by reference in its entirety.

TECHNICAL FIELD

Embodiments of the technology relate, in general, to fermentation technology, and in particular to systems and methods for controlling attenuation in a fermentation process.

BACKGROUND

In recent years, the negative effects of *Saccharomyces cerevisiae* var. *diastaticus* on the brewing community have been highlighted by increasing incidents of beer fermentations being infected with this pernicious beer spoilage yeast. Among different species that are capable of spoiling beer are a group of yeasts that are capable of expressing STA genes, these yeasts are often described as being diastatic. These genes, STA1, STA2, and STA3, allow yeasts to produce glucoamylase enzymes. These enzymes allow the yeast to break down dextrin left behind in the beer after the primary fermentation has consumed the saccharides created in the mashing process. The breakdown of dextrin into smaller mono/di/tri saccharides, which are subsequently fermented, is often referred to as over attenuation or hyper attenuation referring to the drop in the density of the beer as an indirect measurement of the concentration of sugars. Over-attenuation can produce gushing packages and off flavors in the finished product.

Currently, attempts at controlling diastatic yeasts infections are focused around screening and destruction of contaminated product or the wholesale pasteurization of product lines. However, many of the dominant beer styles that are produced in craft breweries are negatively affected by pasteurization. For example, beer styles that have been aggressively hopped post boil, such as India Pale Ales and Pale Ales, will suffer disproportionately from hop oxidation when pasteurized. Even when pasteurization is not prohibited by capital costs, many breweries will opt to not pasteurize their beer as it will cause degradation of the delicate hop aromas. A need exists for methods to stabilize beer brewed in the presence of diastatic yeasts that would otherwise have to be destroyed.

SUMMARY

In an embodiment, a method of controlling attenuation in a fermentation process includes culturing a fungus in a medium to produce a fermented liquid and adding a killer toxin to the fermented liquid. The killer toxin is added in an amount effective to deactivate the fungus.

BRIEF DESCRIPTION OF THE DRAWINGS

The present disclosure will be more readily understood from a detailed description of some example embodiments taken in conjunction with the following figures.

DETAILED DESCRIPTION

Various non-limiting embodiments of the present disclosure will now be described to provide an overall understanding of the principles of the structure, function, and use of the systems and methods disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

Described herein are example embodiments of systems and methods for treating a fermentation product to control or eliminate undesired attenuation of diastatic yeast. Diastatic yeasts are sensitive to killer yeast toxins, such as K1, K2, or K28. In one example embodiment, a killer yeast toxin is added during the fermentation process to deactivate the diastatic yeast thus controlling the attenuation. When the killer yeast toxin is introduced, the *Saccharomyces cerevisiae* var. *diastaticus* is inactivated or stabilized and further attenuation is prevented. Other example embodiments may include the use of killer yeast toxins to control not only diastatic *Saccharomyces* yeasts but also other non-*Saccharomyces* fungi (e.g., *Candida, Dekkera, Aspergillus*) that are vulnerable to these killer yeast toxins. Disclosed herein are methods for controlling over-attenuation of beer or another fermented liquid from microorganisms such as STA+ yeasts (e.g., *Saccharomyces, Dekkera, Brettanomyces*).

The examples discussed herein are examples only and are provided to assist in the explanation of the systems and methods described herein. None of the features or components shown in the drawings or discussed below should be taken as mandatory for any specific implementation of any of these the systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, it should be understood that unless otherwise specified or required by context, any explicit or implicit ordering of steps performed in the execution of a method does not imply that those steps must be performed in the order presented but instead may be performed in a different order or in parallel.

Example embodiments described herein can include introducing a killer yeast toxin directly or indirectly during a fermentation process. For example, in an embodiment, isolated killer yeast toxin may be introduced when the desired level of attenuation has been reached. The killer yeast toxin may be a *Saccharomyces cerevisiae* killer toxin. Examples of the killer yeast toxin include, without limitation, those shown in Table 1 below, and combinations thereof. In an embodiment, more than one toxin at a time may be added, which may increase the effectiveness of the treatment against a wider range of STA+ yeasts. This can be a combination of any of the killer yeast toxins. In some embodiments, the concentration of the toxins in the fermentation batch may be in a range of about $2\times10^3$ to about $4.4\times10^7$ units $ml^{-1}$.

TABLE 1

| Genetic Basis | Yeast Produced Toxin | Toxin Gene Name | Toxic Gene Size (Kbp) | Killer Toxin Name |
|---|---|---|---|---|
| Cytoplasmically inherited encapsulated double-stranded RNA (dsRNA) viruses | | | | |
| *Saccharomyces cerevisiae* | | M1 | 1.8 | K1 |
| | | M2 | 1.5 | K2 |
| | | M28 | 1.9 | K28 |
| *Ustilago maydis* | | M1/M2 | 1.4 | PI |
| | | M2 | 0.98 | P4 |
| | | M2 | 1.2 | P6 |
| *Hanseniaspora uvarum* | | M | | |
| *Phaffia rhodozyma* | | M | | |
| *Zygosaccharomyces bailii* | | M | | |
| Linear double strand plasmids | | | | |
| *Kluyveromyces lactis* | | pGkL1 | 88 | |
| | | pGkL2 | 13.4 | |
| *Pichia acacia* | | pPac 1-1 | 13.6 | |
| | | pPac 1-2 | 6.8 | |
| *Pichia inositovara* | | pPin 1-1 | 18 | |
| | | pPin 1-3 | 10 | |
| Chromosomal genes | | | | |
| *Saccharomyces cerevisiae* | | KHR | 0.9 | KHR |
| | | KHS | 2.1 | KHS |
| *Pichia farinosa* | | SMK1 | 0.6 | KK1 |
| *Pichia membranifaciens* | | | | PMKT |
| | | | | PMKT2 |
| *Williopsis mrakii* | | HMK | | HM-1, K-500 |
| *Williopsis saturnus* | | HSK | | HSK |
| *Williopsis saturnus var mrakii* | | | | WmkT |

In an embodiment where a killer yeast toxin is indirectly introduced, the killer yeast toxin source may be introduced at or prior to the time when the desired level of attenuation has been reached. Killer yeasts are a group of yeasts that carry a viral like particle (VLP) that contains a gene for producing a killer yeast toxin. The killer yeasts may include, without limitation, *S. cerevisiae* strains that produce toxins K1, K2, or K28 or any other killer yeast toxin. In some embodiments, the transfer of the genes from the viral like particles from the killer yeast to a non-killer yeast may occur through protoplast fusion, transformation by plasmid, or by any other means for the purpose of preventing diastatic infections. Example methods of such gene transfer are disclosed in Zimmermann M., Sipiczki M., *Protoplast Fusion of Yeasts*, Nonconventional Yeasts in Biotechnology. Springer, Berlin, Heidelberg (1996), the disclosure of which is incorporated by reference herein in its entirety.

Figure 1:
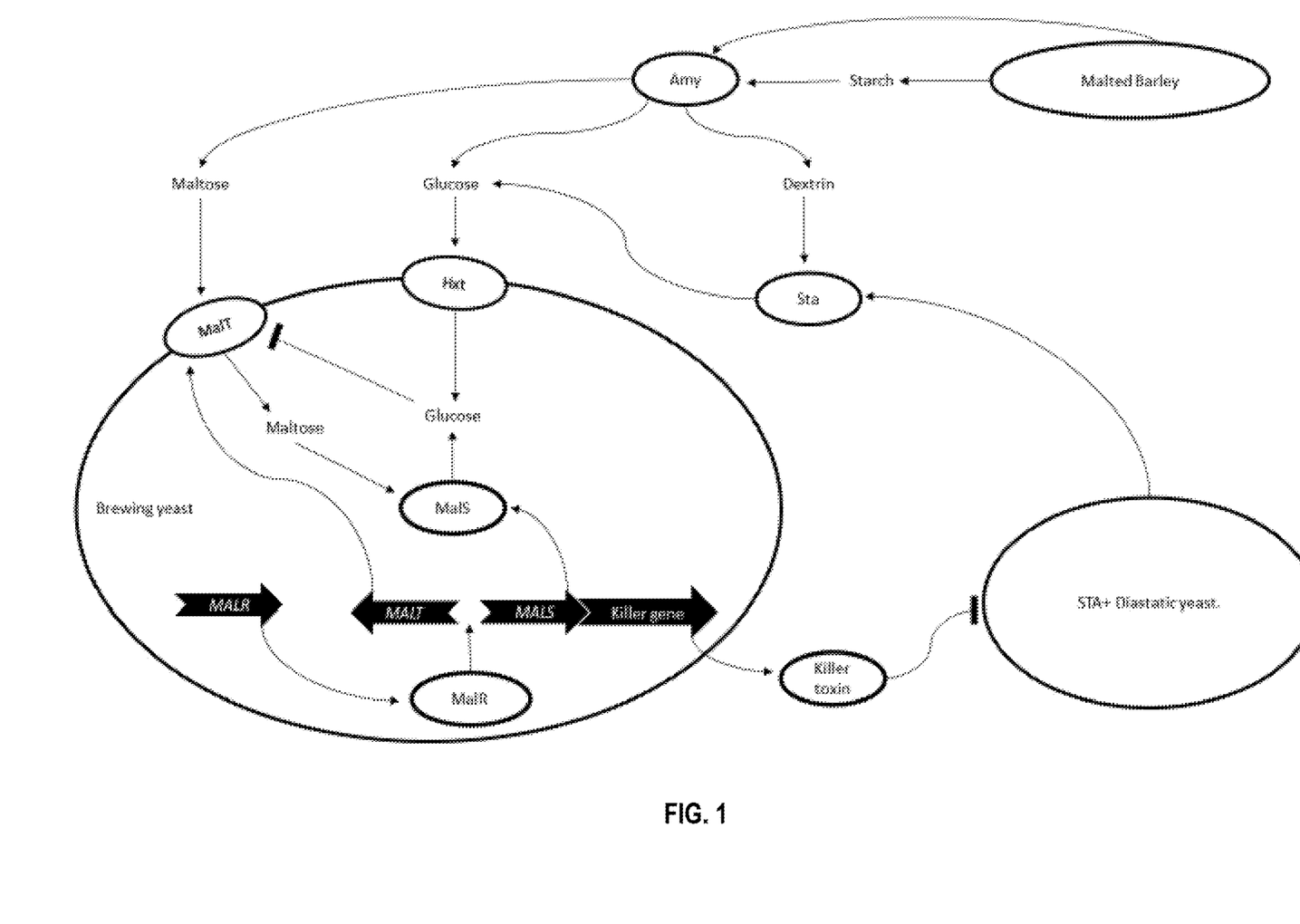
FIG. 1 is a chart showing the change in specific gravity over time during fermentation in the presence of a diastatic yeast.

In another example embodiment, yeast capable of generating a killer yeast toxin is added during the fermentation process to deactivate the diastatic yeast. Various embodiments include a genetically modified host cell capable of producing a killer yeast toxin, where the genetically modified host cell is useful for producing a fermented liquid (e.g., beer). The host cell may be genetically edited, for example, using crispr editing to insert the genes into the chromosome of the non-killer yeast for the purpose of preventing diastatic infections. Example methods of such gene editing are disclosed in Ryan et al., *CRISPR-Cas9 Genome Engineering in Saccharomyces cerevisiae Cells*, Cold Spring Harb. Protoc (2016), the disclosure of which is incorporated herein in its entirety. In some embodiments, the host cell is a brewer's yeast. For example, the gene may be inserted into the maltose regulatory pathway (shown in FIG. 1). When the yeast is exposed to the brewing environment, which includes maltose, the production of the killer yeast toxin begins. An example embodiment provides a method of producing a fermented liquid, comprising: providing a host cell according to an embodiment and culturing said host cell in a suitable medium to produce the fermented liquid, such that the killer yeast toxin is produced to control the attenuation.

In various embodiments, killer yeast toxin may be produced and purified. The killer yeast toxin may then be used to attempt to rescue a fermentation from diastatic yeasts. In an embodiment, a broth of the killer yeast may be grown up and passed across a filter to remove living cells and concentrate the protein. The filtrate containing the protein as well as a number of other constituents may be substantially flavor neutral. The filtrate may also maintain the correct isoelectric point and pH for the specific killer protein being targeted. In some embodiments, the isoelectric point of pH in the fermentation batch after the addition of the toxin is in a range of 3.6 to 5.2 for the proteins to remain stable and in their natively folded confirmation. In some embodiments, yeast protein expression systems, such as those found in *Saccharomyces cerevisiae* and *Picha pastoris*, can be used to produce the protein.

In some embodiments, a method of treating a fermentation product to control or eliminate undesired attenuation of diastatic yeast may include a pre-treatment and/or post-treatment screening assay. The assays may act as an indicator whether treatment with the toxin is likely to have a positive outcome. For example, prior to using the killer yeast toxin for the purpose of clearing the product of any contaminating diastatic yeasts, the yeasts in the fermenter may be screened for the presence of genetic pathways that might confer resistance to the yeast to the killer yeast toxin. Example target genes for resistance screening to the K2 toxin include, without limitation: Beta glucan synthesis and assembly (THP1, KRE6, FKE1, SMI1, AIM26, TRS65, ANP1); N/O-linked protein glycosylation (OST3, PMT1, PMT2, ALG8, AMP1); Membrane organization and function (DRS2, LEM3, IGR1); and Cell cycle growth and proliferation (ELM1, CKA2, EGT2). Example target genes for sensitivity screening to the K2 toxin include, without limitation: General stress response/HOG pathway (HOG1, BEM2, BNI1, FUS3, RLM1); Cell wall biogenesis (LRG1, BEM2, BNI1, FUS3); and Phosoinositide synthesis (PLC1 and SAC1).

Figure 2:
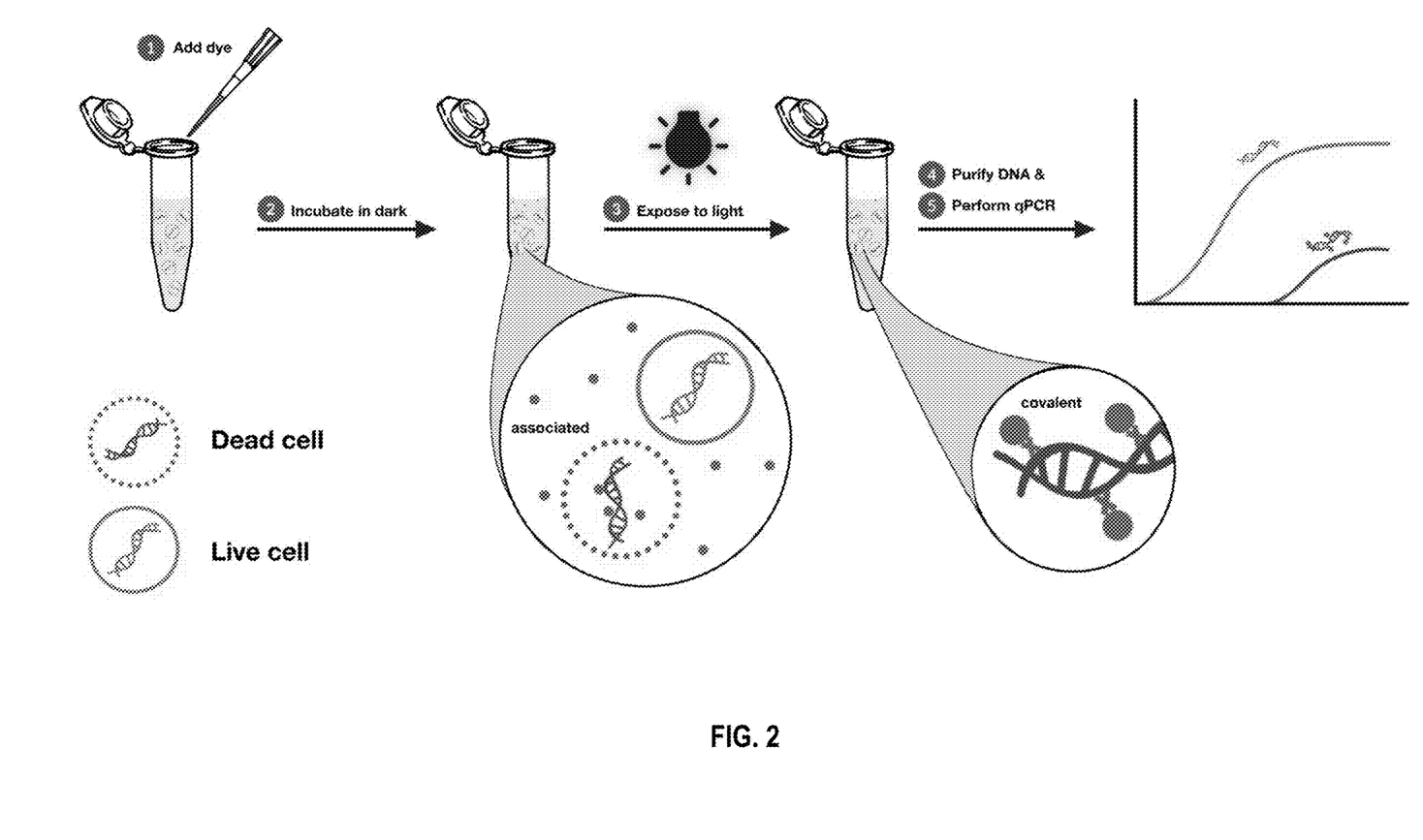
FIG. 2 is a schematic showing a method of a post-screening assay according to an embodiment.

In an embodiment, after the killer yeast toxin is added, a post-treatment screen may include a viability PCR assay to ensure the product is clear of any remaining viable diastatic yeast cells. An understanding of the final community composition of the fermentation may be used to determine the efficacy of the treatment. Culture dependent methods such as cell counts lack the ability to distinguish between STA+ and STA-cells. Direct methods such as plate counts on media such as PFDM and LCSM time consuming and have been historically troubled by false positives. PCR primers for the STA family of genes will be used in conjunction with the PMAxx dye and a qPCR thermocycler to determine if any remaining viable STA1+ yeast cells are remaining as illustrated in FIG. 2. Example methods are disclosed in Emerson, J. B. et al., *Schrödinger's microbes: Tools for distinguishing the living from the dead in microbial ecosystems*, Microbiome, 5(1), 86 (2017), the disclosure of which is incorporated by reference herein in its entirety.

Figure 5:
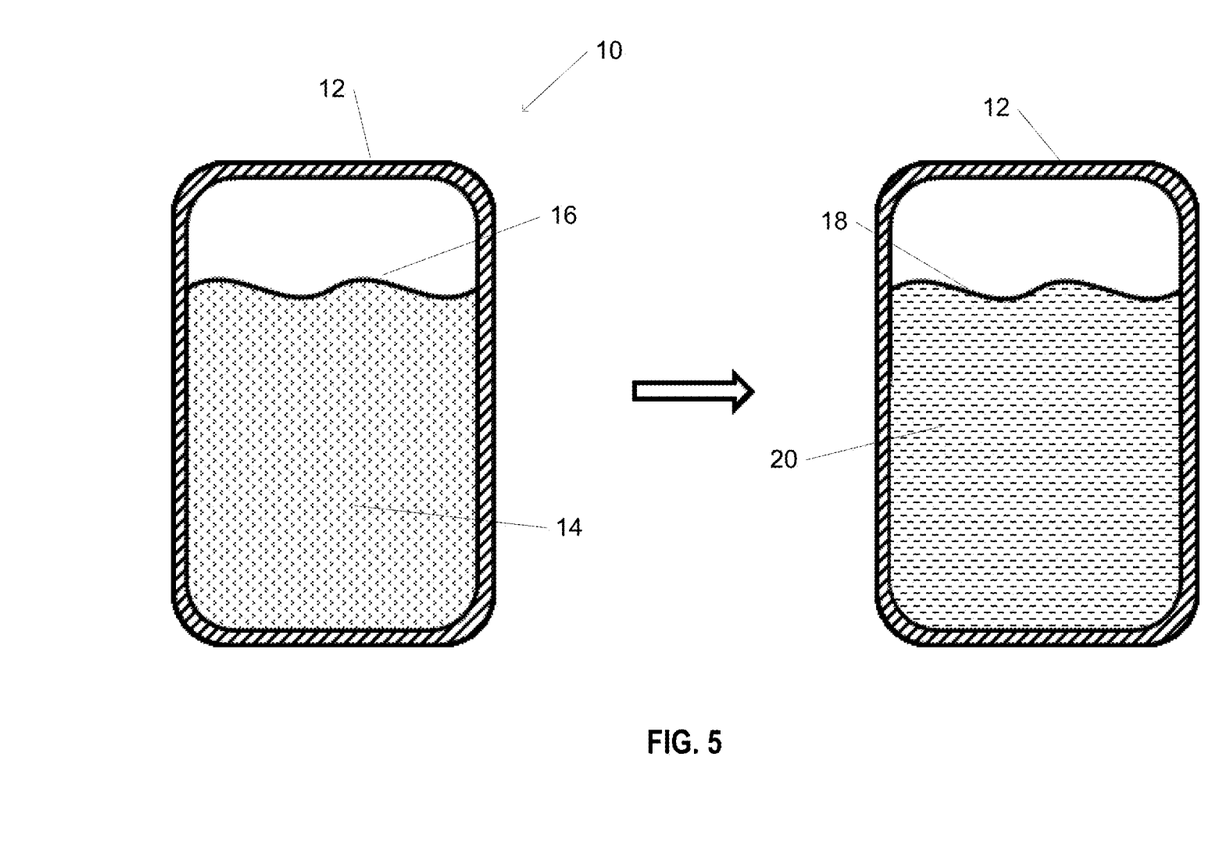
FIG. 5 depicts a system according to an embodiment before and after fermentation.

Example embodiments described herein can include a system for controlling attenuation in a fermentation process. For example, as shown in FIG. 5, the system 10 may include a fermentation system 12 configured to culture a fungus 14 in a medium 16 to produce a fermented liquid 18. The system 10 may include a killer toxin 20 configured to be added to the fermented liquid in an amount effective to deactivate the fungus 14.

The following examples are provided to help illustrate the present invention and are not comprehensive or limiting in any manner.

Example 1

Figure 3:
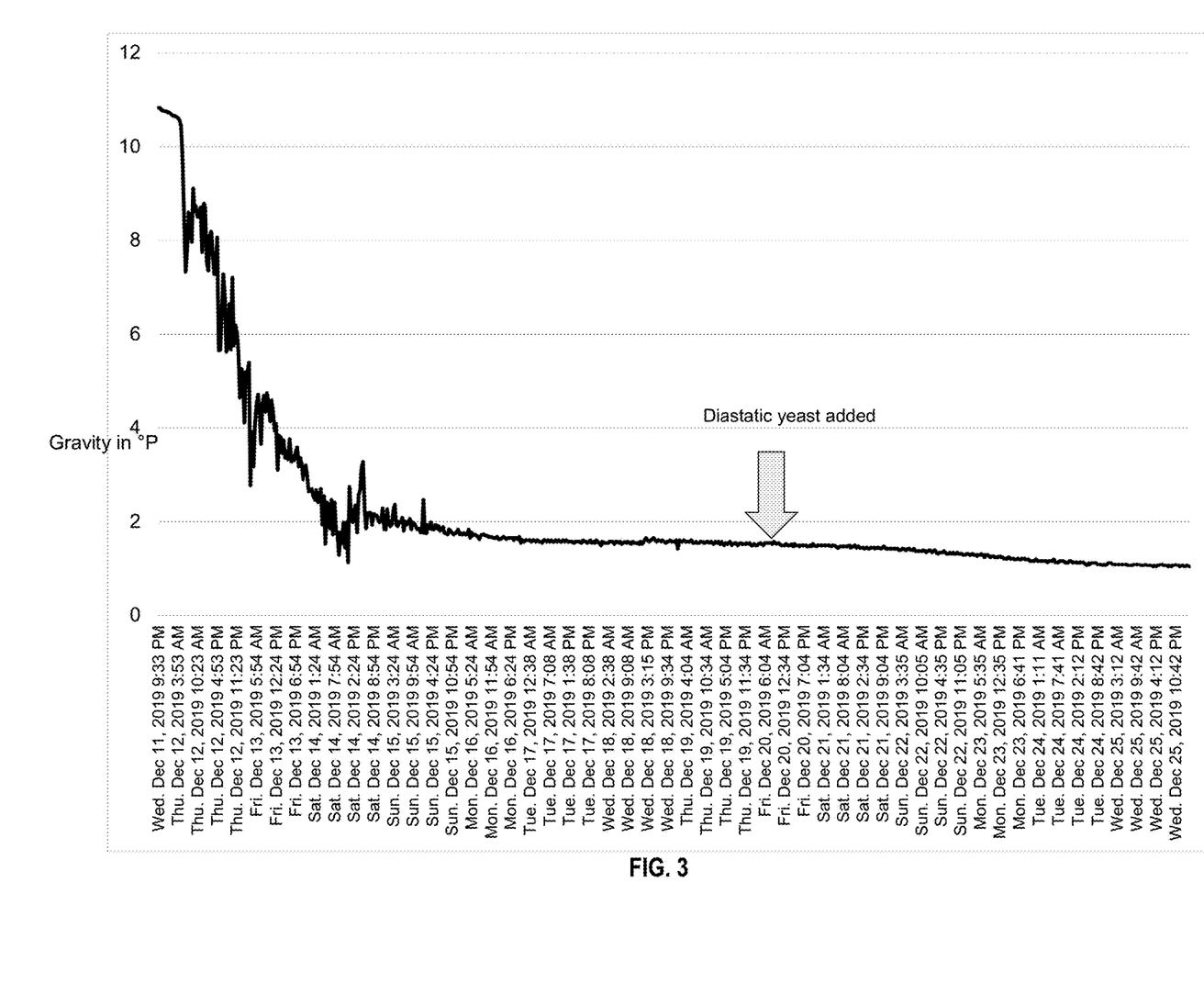
FIGS. 3 and 4 are charts showing the change in specific gravity over time during fermentation in the presence of a diastatic yeast with and without the presence of a killer yeast toxin, respectively.
Figure 4:
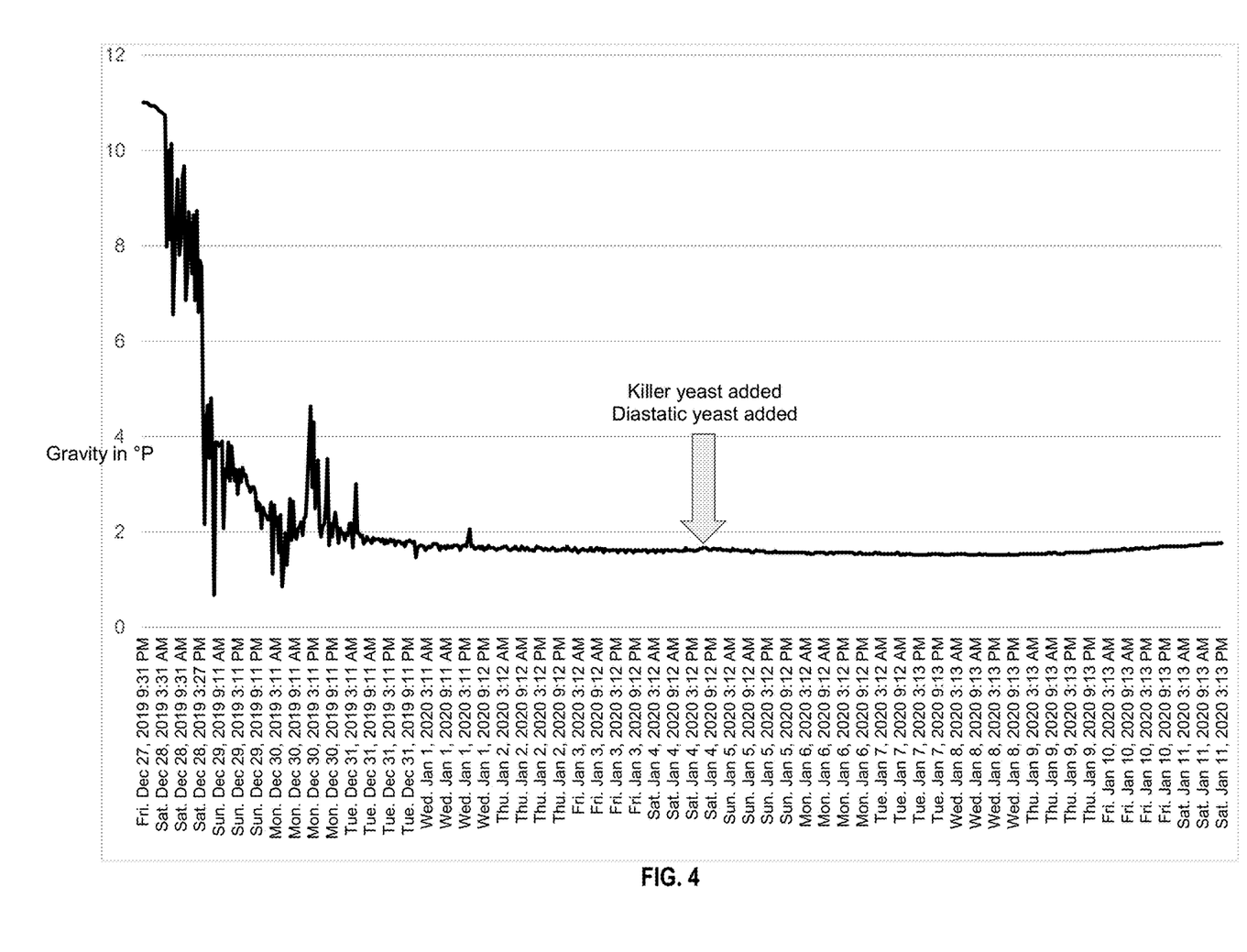

Two tests were completed in which 10,000 liters of beer were produced in each test. Using real time data collection via inline densitometer, samples were taken every 30 minutes with a total of 681 samples. As an indicator for attenuation, the specific gravity of the samples was recorded. FIGS. 3 and 4 show the specific gravity (degrees Plato) over time in Trial 1 and Trial 2, respectively.

When the specific gravity leveled off or became terminal, diastatic yeast was added. In Trial 2, killer yeast capable of producing the killer yeast toxin K2 was added at the same time as the diastatic yeast. As seen in FIG. 3, the specific gravity began dropping after the addition of the diastatic yeast in Trial 1. In contrast, as seen in FIG. 4, the specific gravity remained relatively level in Trial 2 indicating that the diastatic yeast was deactivated. There is a slight increase in the specific gravity in FIG. 4, which was attributed to the escape of ethanol while the diastatic yeast and killer yeast were added. The results show that superattuation was eliminated when the diastatic yeast was exposed to the killer yeast toxin K2 during the fermentation process.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. A method of controlling attenuation in a fermentation process comprising:
   culturing a fungus in a medium to produce beer, wherein the fungus is at least one of *Saccharomyces, Dekkera, Brettanomyce, Candida*, or *Aspergillus*;
   adding a killer toxin to the beer, wherein the killer toxin is added in an amount effective to deactivate the fungus;
   conducting a first screening assay on the beer before adding the killer toxin; and
   conducting a second screening assay on the beer after adding the killer toxin.

2. The method of claim 1, wherein adding the killer toxin comprises adding the killer toxin when a desired level of attenuation has been reached.

3. The method of claim 1, wherein adding the killer toxin comprises adding more than one type of killer toxin.

4. The method of claim 1, wherein adding the killer toxin comprises directly adding the killer toxin to the beer.

5. The method of claim 4, the method further comprising, before the killer toxin is added:
   producing a broth by a killer yeast capable of generating the killer toxin; and
   filtering the broth to provide the killer toxin.

6. The method of claim 1, wherein adding the killer toxin comprises indirectly adding the killer toxin to the beer.

7. The method of claim 6, wherein indirectly adding the killer toxin comprises adding viral like particles (VLPs) that contain a gene for producing the killer toxin.

8. The method of claim 7, wherein adding the VLPs comprises adding a killer yeast to the beer, wherein the killer yeast carries the VLPs.

9. The method of claim 6, wherein indirectly adding the killer toxin comprises adding a killer yeast capable of generating the killer toxin.

10. The method of claim 1, wherein the first screening assay detects whether the fungus includes a genetic pathway that confers resistance to the killer toxin.

11. The method of claim 1, wherein the second screening assay detects a presence of remaining viable fungus cells.

12. The method of claim 1, wherein the killer toxin is at least one of K1, K2, or K28.

* * * * *